(12) United States Patent
Wagner et al.

(10) Patent No.: US 6,395,689 B1
(45) Date of Patent: May 28, 2002

(54) TERPENE ETHERS AND THEIR USE

(75) Inventors: Adalbert Wagner, Gersthofen; Frank Ebmeyer, Lüneburg; Georg Stuhlmüller, Gablingen; Maximilian Simon, Olching; Herbert Vojacek, Gmund, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/272,838

(22) Filed: Mar. 19, 1999

(30) Foreign Application Priority Data

Mar. 20, 1998 (DE) .......................... 198 12 245

(51) Int. Cl.⁷ .......................... C10M 105/18
(52) U.S. Cl. .......................... 508/580; 252/73
(58) Field of Search .................. 568/666, 612, 568/606, 664, 665, 670; 252/1, 73; 512/19; 508/580

(56) References Cited

U.S. PATENT DOCUMENTS

| | | | | |
|---|---|---|---|---|
| 4,521,324 A | | 6/1985 | Tsubouchi et al. ............ | 252/73 |
| 4,590,302 A | | 5/1986 | Scheidl et al. ............... | 568/665 |
| 4,609,481 A | | 9/1986 | Tsubouchi et al. ............ | 252/73 |
| 4,759,860 A | * | 7/1988 | Tanaka et al. ............... | 252/32.5 |
| 4,922,047 A | | 5/1990 | Chen et al. ................... | 585/12 |
| 5,366,959 A | | 11/1994 | Boden et al. ................. | 512/19 |

FOREIGN PATENT DOCUMENTS

| | | |
|---|---|---|
| DE | 1644926 | 8/1970 |
| DE | 3321773 | 12/1983 |
| DE | 3337503 | 4/1984 |
| DE | 3327014 | 2/1985 |
| EP | 0082967 | 7/1983 |
| EP | 0319580 | 6/1989 |
| GB | 1190836 | 5/1970 |

OTHER PUBLICATIONS

EPO Search Report, Jun. 1999.
XP–002105709, "Terpene Ethers, Part VI, Synthesis of Terpene Ethers Of Polyethylene Glycols," S. Kucharski and B. Burczyk, Roczniki Chemii, Bd. 45, Nr. 3, 1971, pp. 479–484.
XP–002015710, "Surfactants containing terpenyl group. VI. Snythesis and their surface activities of polyethylene glycol monoterpenyl ethers from various terpene hydrcarbons and polyethylene glycols." Chemical Abstracts, vol. 82, No. 18, May 5, 1975, Abstract No. 113479z.

* cited by examiner

*Primary Examiner*—Rosalynd Keys
(74) *Attorney, Agent, or Firm*—Susan S. Jackson; Scott E. Hanf

(57) ABSTRACT

The present invention relates to terpene ethers of the general formula (I)

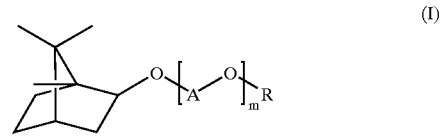

in which the substituents have the meanings defined in the description, to a process for their preparation and to their use.

The novel terpene ethers are suitable as traction fluids, as fragrances, as solvents and as reactive intermediates.

3 Claims, No Drawings

TERPENE ETHERS AND THEIR USE

BACKGROUND OF THE INVENTION

Lubricated traction gears require special power transmission fluids which transmit the torque of the driving part to the driven part by means of friction. The lubricating film in the contact zone between the two roller members is subjected to shearing by the transmitted frictional forces.

The profile of requirements for traction fluids comprises, inter alia, good low-temperature flow behavior and sufficient viscosity at operation temperature sufficiently high coefficient of friction over the operation temperature range low evaporation losses.

EP-A-082 967 describes organic compounds for use as fluid for the transmission of frictional forces. DE-A-3 321 773 and DE-A-3 337 503 describe cyclic hydrocarbons for use as fluid for traction drive means. DE 1 644 926 describes condensed saturated hydrocarbons as traction fluid. Furthermore, EP-A-319 580 mentions hydrocarbon diesters for use as traction fluids. DE-A-3 327 014 describes terpene ethers.

DE-A-3 327 014 describes, inter alia, Example 6 (here, referred to below as Comparative Example 1).

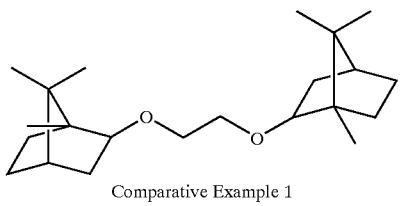

Comparative Example 1

Comparative Example 1 tends to crystallize on prolonged standing, has a melting point of from 72 to 75° C. and thus does not meet the requirements for good low-temperature behavior. For use as traction fluid, the solidification points must be substantially below −20° C.

SUMMARY OF THE INVENTION

It was thus the object of the present invention to provide novel compounds having improved low-temperature behavior.

Surprisingly, it was found that certain terpene ethers, in spite of higher molecular weights, nevertheless have substantially lower solidification points and thus meet the criterion of low-temperature flowability.

The invention relates to novel terpene ethers, a process for their preparation and their use, inter alia, as traction fluids or in the area of fragrances and solvents.

The invention thus relates to novel terpene ethers of the general formula I

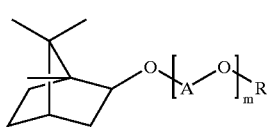

(I)

in which
  m is a number from 2 to 5,
  A is a branched or straight-chain alkylene group having 2 to 5 carbon atoms, R is hydrogen,
  $C_8$–$C_4$-alkyl, which is optionally substituted by $C_5$–$C_{12}$-cycloalkyl, by $C_7$–$C_{12}$-bicycloalkyl or by $C_8$–$C_{11}$-tricycloalkyl, it being possible for the cycloalkyl radical or the tricycloalkyl radical to carry a substituent —$CH_2$—O—$R^1$, or it being possible for the cycloalkyl radical to be substituted by a radical —O—$R^1$,
  $C_5$–$C_{12}$-cycloalkyl, which may be substituted by a radical —O—$R^1$,
  $C_7$–$C_{12}$-bicycloalkyl, or
  $C_8$–$C_{12}$-tricycloalkyl,
$R^1$ being hydrogen,
  $C_1$–$C_{18}$-alkyl,
  $C_5$–$C_{12}$-cycloalkyl,
  $C_7$–$C_{12}$-bicycloalkyl, or
  cycloalkyl-, bicycloalkyl- or tricycloalkyl-substituted $C_1$–$C_6$-alkyl.

It has also surprisingly been found that these novel terpene ethers have at least an equally high coefficient of friction as, in some cases even a higher coefficient of friction than, Comparative Example 1. This contradicts all expectations based on systematic friction measurements using model substances (literature: Dokumentation des BMFT: Tribologie [BMFT Documentation: Tribology] Vol. 2, published by Springer Verlag Berlin, Heidelberg, N.Y., 1982, pages 281–313). According to this, a decrease in the coefficient of friction under elastohydrodynamic operating conditions would be expected with increasing chain length of the ether bridge between the isobornyl radicals, owing to the associated decrease in the steric hindrance.

DESCRIPTION OF THE PREFERRED EMBODIMENTS

Compounds of the formula (I) in which A is a straight-chain or branched alkylene chain having 2–5 carbon atoms, m is 2 or 3 and R has the meaning of one of the radicals mentioned below: hydrogen, alkyl having 3–5 carbon atoms, cycloalkyl having 5–12 carbon atoms, bicycloalkyl having 7–12 carbon atoms and tricycloalkyl having 8–12 carbon atoms are preferred.

Compounds of the formula (I) in which m is 2 or 3 and R is hydrogen or $C_7$–$C_{12}$-bicycloalkyl are very particularly preferred.

In the terpene ethers according to the invention—according to IUPAC nomenclature 1,7,7-trimethylbicyclo[2.2.1]hept-2-yl ethers (=isobornyl ethers) the 1,7,7-trimethylbicyclo[2.2.1]hept-2-yl radical may be in the d or l form, preferably in the form of the racemate and the radical

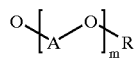

in the exo and/or endo form.

The novel compounds can be prepared by methods known per se.

The preferred procedure for the preparation of the novel ethers starts from camphene, which is reacted with the alcohols of the general formula

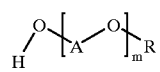

in which R has the abovementioned meaning. In the reaction taking place in the presence of acidic catalysts according to the equation:

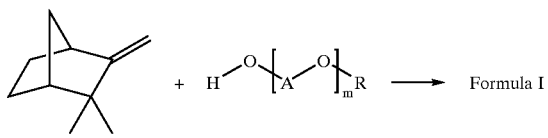

the camphene undergoes an intermediate Wagner-Meerwein rearrangement reaction to give a camphene intermediate.

The synthesis is carried out at temperatures between room temperature (20° C.) and 160° C., preferably at from 50 to 140° C. and in particular at from 70 to 120° C. Depending on the desired product, the reactants can be used in equimolar amounts or an excess of one or other reactant can be employed. An excess of camphene proved advantageous for the synthesis of diisobornyl ethers.

Catalysts used are mineral acids, such as sulfuric acid, perchloric acid, phosphoric acid, chlorosulfonic acid, etc., strong organic acids, such as p-toluenesulfonic acid, methanesulfonic acid and camphor-10-sulfonic acid, acidic ion exchangers or Friedel-Crafts catalysts, such as boron trifluoride and its adducts (e.g. etherates, glacial acetic acid complex), aluminum chloride, zinc chloride, $PdCl_2$, $Pd(OAc)_2$, $SbCl_3$, $SbCl_5$, $YtCl_3$, $LaCl_3$, zeolites and others, in amounts of from 0.1 to 10, preferably from 0.5 to 6 and in particular from 1 to 4, % by weight, based on camphene used.

The reaction can be carried out in the presence or in the absence of inert solvents. Suitable solvents are, for example, aliphatic hydrocarbons such as pentane, hexane, naphtha fractions, chloroform or carbon tetrachloride, aromatic hydrocarbons such as toluene, xylene or chlorobenzene, cycloaliphatic hydrocarbons, such as cyclohexane or cyclooctane, or ethers, such as dioxane, dibutyl ether or ethylene glycol dimethyl ether. The procedure without the addition of solvent is particularly advisable.

In the reaction, in general, all reactants can be initially introduced in their total amount, including the catalyst. In some cases, the reaction takes place slightly exothermally so that in this case it is advantageous initially to introduce the catalyst and the alcohol and to add the camphene at the desired temperature.

Diethylene glycol, triethylene glycol, dipropylene glycol and tripropylene glycol are particularly preferred as examples of alcohols which are reacted with camphene.

The purification of the reaction products is carried out in general after removal of the catalyst (e.g. washing with water or neutralization by means of bases or simple filtration) by distillation, but for some intended uses a distillation is not necessary. A further possibility for purification is recrystallization from suitable solvents.

The preferred reaction products are low-viscosity to high-viscosity liquids which are colorless to faintly yellow.

As already mentioned, the novel compounds are surprisingly distinguished by the fact that, in comparison with Comparative Example 1 (Example 6 from DE-A-332 701 A 1), they do not solidify down to −30° C. When they are used as traction fluids, the compounds described can be employed alone or as mixtures with other substances, with the main proportion of these mixtures comprising one or more of the compounds described here.

In the traction fluid, the terpene ether is used in a concentration of at least 5% by weight, preferably in a concentration of from 20 to 95% by weight.

Some of the novel compounds have a pronounced fragrance character and can therefore be used alone as fragrances or in a fragrance combination, i.e. in mixtures with synthetic and natural oils, alcohols, aldehydes, ketones or esters, and they are furthermore suitable for perfuming soaps, detergents, powders, bath oils, hair cosmetics, creams and further known fragrance-containing formulations. Owing to their consistency, a major part of the novel terpene ethers is of interest as fixing agents for fragrances, and the compounds suitable for this purpose are viscous liquids and therefore have the property of greatly reducing the volatility of fragrances. Furthermore, some of the products can be used as solvents, for example for resins and coating materials.

Finally, those members of the novel ethers which have a free hydroxyl group are suitable as reactive intermediates, for example for the synthesis of crop protection agents, pesticides and drugs.

EXAMPLES

Table 1 summarizes the compounds prepared by the general method described below, for illustrating the invention.

General method for synthesizing terpene ethers.

Catalyst is added to 1 mol of the corresponding dry alcohol and the mixture is heated to 80° C. until the suspension is stirrable, and molten technical-grade camphene is then added dropwise. Stirring is then carried out for 24 h at 80° C. Thereafter, water is added at 80° C. to decompose the catalyst, stirring is effected for 30 min and the aqueous phase is then separated off. This process is repeated once more. The unreacted camphene is removed by means of steam distillation. The oil bath is heated to 140° C. for this purpose. The condensate is analyzed by GC. To remove residual water and low-boiling byproducts, the residue is heated to 170° C. in a vacuum at 40 mbar. After foam formation has died down, the solution is filtered through a folded filter, the product, comprising mono- and diisobornyl ether, being obtained as a low-viscosity oil. Mono- and diether can be separated by subsequent distillation.

TABLE 1

Synthesis of terpene ethers

| Alcohol | Product | Equivalent of camphene | Catalyst (equivalents) | B.p. ° C. (pressure) | M.p. | Molar mass** (M + H) |
|---|---|---|---|---|---|---|
| Ethylene glycol | Ethylene glycol diisobornyl ether Comparative Example 1 | 3* | AlCl3 (0.037) | 168–169 (1.3 mbar) | 72–75° C. | — |

TABLE 1-continued

Synthesis of terpene ethers

| Alcohol | Product | Equivalent of camphene | Catalyst (equivalents) | B.p. ° C. (pressure) | M.p. | Molar mass** (M + H) |
|---|---|---|---|---|---|---|
| Diethylene glycol | Diethylene glycol isobornyl ether Example 1 | 4 | BF3—2CH3CO2H (0.037) | n.d. | <−30° C. | 243 |
| Diethylene glycol | Diethylene glycol diisobornyl ether Example 1a | 4 | BF3—2CH3CO2H (0.037) | n.d. | <−30° C. | 379 |
| Triethylene glycol | Triethylene glycol isobornyl ether Example 2 | 4 | BF3—2CH3CO2H (0.037) | 148–152 (0.4 mmHg) | <−30° C. | 287 |
| Triethylene glycol | Triethylene glycol diisobornyl ether Example 2a | 4 | BF3—2CH3CO2H (0.037) | 184 (0.1 mmHg) | <−30° C. | 423 |
| 1,2-Dipropylene glycol | 1,2-Dipropylene glycol isobornyl ether Example 3 | 4 | BF3—2CH3CO2H (0.037) | n.d. | <−30° C. | 271 |
| 1,2-Dipropylene glycol | 1,2-Dipropylene glycol diisobornyl ether Example 3a | 4 | BF3—2CH3CO2H (0.037) | 177 (0.4 bar) | <−30° C. | 407 |
| 1,2-Tripropylene glycol | 1,2-Tripropylene glycol isobornyl ether Example 4 | 4 | BF3—2CH3CO2H (0.037) | 147 (0.4 mmHg) | <−30° C. | 329 |
| 1,2-Tripropylene glycol | 1,2-Tripropylene glycol diisobornyl ether Example 4a | 4 | BF3—2CH3CO2H (0.037) | 193 (0.4 mmHg) | <−30° C. | 465 |

*Toluene as solvent
**Mass spectrum DCI (Desorption Chemical Ionization)
n.d. not determined since fraction was contaminated with byproducts Table 2

Coefficients of Friction of Model Substances of Variable Chain Length

The friction measurement was carried out on a two-disk deskstand as described in the publication cited on page 2. Mean values of the coefficients of friction were compared with the following limits of the operating parameters.

Mean Hertsch pressure $p_m = 500 \ldots 1260$ N/mm$^2$

Circumferential velocity $v = 0.42 \ldots 8.4$ m/s

Slip s less than 6%

Temperature T=50° C.

Roughness of the friction body surfaces corresponding to that of conventional friction gear designs.

| | Model substance | Mean coefficient of friction |
|---|---|---|
| A1 | (cyclohexyl)-O-(cyclohexyl) | 0.086 |
| A2 | (cyclohexyl)-CH2-O-CH2-(cyclohexyl) | 0.076 |
| A3 | (cyclohexyl)-CH2-O-CH2-O-CH2-(cyclohexyl) | 0.075 |
| B1 | (cyclohexyl)-(cyclohexyl) | 0.08 |
| B2 | (cyclohexyl)-CH2-CH2-(cyclohexyl) | 0.078 |
| C1 | H-O-CH2-CH2-O-H | 0.017 |

| Model substance | | Mean coefficient of friction |
|---|---|---|
| C2 | H-O-CH₂-CH₂-O-CH₂-CH₂-O-H | 0.016 |
| C3 | H-O-CH₂-CH₂-O-CH₂-CH₂-O-CH₂-CH₂-O-H | 0.015 |
| Comparative Example 1 | Ethylene glycol diisobornyl ether | 0.094 |
| Ex. 1a | Diethylene glycol diisobornyl ether | 0.090 |
| Ex. 2a | Triethylene glycol diisobornyl ether | 0.068 |
| Ex. 3a | Dipropylene glycol diisobornyl ether | 0.099 |
| Ex. 4a | Tripropylene glycol diisobornyl ether | 0.086 |

What is claimed is:

1. A traction fluid for use in traction gears comprising a terpene ether of formula (I)

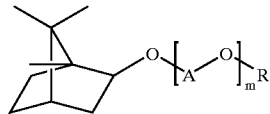

(I)

in which
  m is a number from 2 to 5,
  A is a branched alkylene group having 3 carbon atoms, and
  R is hydrogen or $C_7$–$C_{12}$-bicycloalkyl, or a mixture of terpene ethers comprising the terpene ether of the formula (I), wherein the terpene ether of the formula (I) or the mixture of terpene ethers is used alone or in a mixture with other traction fluids.

2. The traction fluid as claimed in claim 1, wherein the terpene ether is used in a concentration of at least 5% by weight.

3. The traction fluid as claimed in claim 2, wherein the terpene ether is used in a concentration of from 20 to 95% by weight.

* * * * *